(12) United States Patent
Okazoe et al.

(10) Patent No.: US 6,969,776 B2
(45) Date of Patent: Nov. 29, 2005

(54) PROCESS FOR PRODUCING FLUORINATED KETONE

(75) Inventors: Takashi Okazoe, Kanagawa (JP); Kunio Watanabe, Kanagawa (JP); Masahiro Ito, Kanagawa (JP); Daisuke Shirakawa, Kanagawa (JP); Shin Tatematsu, Kanagawa (JP); Hirokazu Takagi, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/869,053

(22) Filed: Jun. 17, 2004

(65) Prior Publication Data

US 2004/0267053 A1 Dec. 30, 2004

Related U.S. Application Data

(63) Continuation of application No. 10/372,765, filed on Feb. 26, 2003, now Pat. No. 6,803,488, which is a continuation of application No. PCT/JP01/07495, filed on Aug. 30, 2001.

(30) Foreign Application Priority Data

Aug. 30, 2000 (JP) ........................................ 2000-261118

(51) Int. Cl.$^7$ .................... C07C 45/65; C07C 43/30; C07C 53/38; C07C 51/58
(52) U.S. Cl. ...................... 568/347; 568/348; 568/354; 568/364; 568/391; 568/393; 568/600; 568/604; 562/849; 562/852
(58) Field of Search ................. 568/347, 348, 568/354, 364, 391, 393, 600, 604; 562/849, 852

(56) References Cited

U.S. PATENT DOCUMENTS

| | | | |
|---|---|---|---|
| 3,900,372 A | 8/1975 | Childs et al. .................. | 204/81 |
| 5,093,432 A | 3/1992 | Bierschenk et al. ..... | 525/331.6 |
| 5,322,903 A | 6/1994 | Bierschenk et al. ..... | 525/331.6 |
| 5,466,877 A | 11/1995 | Moore ........................ | 502/852 |
| 6,255,536 B1 | 7/2001 | Worm et al. ................ | 568/615 |

FOREIGN PATENT DOCUMENTS

| | | |
|---|---|---|
| EP | 0 062 430 | 10/1982 |
| EP | 0 150 618 | 8/1985 |
| JP | 52-010221 | 1/1977 |
| JP | 2-311438 | 12/1990 |
| JP | 2001-139509 | 5/2001 |
| WO | WO 95/25082 | 9/1995 |
| WO | WO 00/56694 | 9/2000 |
| WO | WO 02/10107 | 2/2002 |
| WO | WO 02/10108 | 2/2002 |
| WO | WO 02/44138 | 6/2002 |
| WO | WO 02/055471 | 7/2002 |

OTHER PUBLICATIONS

Koichi Murata et al, "The Thermal Decomposition of Perfluoroesters," *J. AM. Chem. Soc.*, 1998, 120, 7118.
Tatarinova, E. L., et al. "Reaction of hexafluoropropene oxide dimer with water and alcohols", Database accession No. 1993:212088, XP002323680.
Tatarinova, E. L., et al. "Reaction of hexafluoropropene oxide trimer with water and alcohols", Database accession No. 1993:59265, XP002323681.

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

The present invention provides a process whereby fluorinated ketones of various structures can be produced by short process steps and which is useful as an industrial production process.

Namely, it is a process for producing a fluorinated ketone of the following formula (5), which comprises reacting a compound of the following formula (3) having a fluorine content of at least 30 mass %, with fluorine in a liquid phase to obtain a compound of the following formula (4), and then, subjecting the ester linkage of the compound of the formula (4) to a dissociation reaction:

$$R^C COOCHR^A R^B \quad (3)$$

$$R^{CF} COOCFR^{AF} R^{BF} \quad (4)$$

$$R^{AF} R^{BF} C = O \quad (5)$$

wherein each of $R^A$ and $R^{AF}$ are each a monovalent organic group such as an alkyl group, or $R^A$ and $R^B$ may be bonded to each other to form a bivalent organic group such as an alkylene group, $R^{AF}$ and $R^{BF}$ are a monovalent organic group such as a perfluoroalkyl group formed by fluorination of $R^A$ and $R^B$, or they are bonded to each other to form a bivalent organic group such as a perfluoroalkylene group, and $R^C$ and $R^{CF}$ are each a monovalent organic group such as a perfluoroalkyl group which may contain an etheric oxygen atom.

23 Claims, No Drawings

PROCESS FOR PRODUCING FLUORINATED KETONE

This is a continuation application of U.S. application Ser. No. 10/372,765 filed on Feb. 26, 2003, now U.S. Pat. No. 6,803,488 which is a continuation of the International Application No. PCT/JP01/07495, filed Aug. 30, 2001.

TECHNICAL FIELD

The present invention relates to an industrially useful process for producing a fluorinated ketone.

BACKGROUND ART

Heretofore, as a method for fluorinating all of C—H portions in a C—H containing compound to C—F, a method of employing cobalt trifluoride, a method for direct fluorination by means of fluorine gas, or a method of carrying out a fluorination reaction by using, as a fluorine source, hydrogen fluoride formed by electrolysis in an electritic cell (electrochemical fluorination, hereinafter referred to as ECF method), has been known. The method of employing cobalt trifluoride is one wherein the reaction is carried out by a gas-solid reaction at a high temperature, whereby there is a problem such that isomerization or bond breakage is likely to take place, to form various types of by-products. While, the fluorination reaction by ECF method has had a problem such that an isomerization reaction takes place, or a problem such that breakage of the main chain or a rebonding reaction is likely to take place, and thus has had a problem that the desired compound can not be obtained with good purity.

In a case where a fluorination reaction is carried out by means of fluorine gas, a method of carrying out the reaction in a gas phase and a method of carrying out the reaction in a liquid phase, are known. However, the gas phase reaction has a problem such that breakage of C—C single bonds takes place during the fluorination reaction to form various types of by-products. In recent years, a method of carrying out the reaction in a liquid phase has been reported. For example, a method of carrying out fluorination in a liquid phase by reacting fluorine gas to a non-fluorinated compound in a liquid phase (U.S. Pat. No. 5,093,432), has been reported. Further, a method for obtaining an acid fluoride compound by pyrolyzing a perfluorinated ester compound, is also known, and it is disclosed that such a compound can be obtained by directly fluorinating a hydrocarbon type ester compound having the corresponding structure by means of fluorine gas in a liquid phase (J. Am. Chem. Soc., 120, 7117 (1998)).

In a case where a fluorination reaction is carried out by means of fluorine gas in a liquid phase, it is common to employ a solvent capable of dissolving fluorine gas, as the solvent of the reaction. However, a hydrocarbon compound as the starting material in the conventional method usually has a low solubility to a solvent which is commonly used for the fluorination reaction. Accordingly, the reaction is carried out at a very low concentration, whereby there has been a problem that the production efficiency is poor, or the reaction will be a reaction in a suspension system which is rather disadvantageous. Further, if it is attempted to directly fluorinate a low molecular weight hydrocarbon compound like one having a molecular weight of less than 200, in a liquid phase, there has been a problem that the yield in the reaction tends to be remarkably low.

On the other hand, as a method for producing a fluorinated ketone, a method is known wherein a partially fluorinated ester is perfluorinated by ECF method, followed by a dissociation reaction to obtain a fluorinated ketone (U.S. Pat. No. 3,900,372). However, the method employing ECF method has the above-mentioned drawbacks and a problem that the yield is low. Especially when an etheric oxygen atom is present in the structure of the compound, there has been a drawback that due to the cleavage of the C—O bond, the yield in the fluorination reaction tends to be extremely low.

Further, a method for obtaining a ketone by dissociating a perfluoroester, is known (U.S. Pat. No. 5,466,877). However, if a fluorination reaction is employed for the step of producing a perfluoroester in the method, there has been a problem that supply of the ester tends to fail, or the reaction system tends to be non-uniform.

It is an object of the present invention to provide an industrial process, whereby a fluorinated ketone can be produced efficiently and at a low cost.

DISCLOSURE OF THE INVENTION

In the present invention, as a result of various studies on causes of the problems of the conventional methods, attention has been drawn to the drawbacks in a fluorination reaction in a liquid phase such that if a conventional hydrocarbon compound is used as a substrate for the fluorination reaction, the solubility in the liquid phase used for the fluorination reaction is low, and if the substrate for the fluorination reaction is of a low molecular weight, the boiling point of the substrate tends to be low, so that the reaction of fluorine with the substrate is likely to take place in a gas phase, and a decomposition reaction will take place.

Accordingly, from a compound which is available at a low cost, an ester compound (3) having a specific structure, which has a high molecular weight to such an extent that a gas phase reaction hardly takes place and which has fluorine atoms introduced so that it will be soluble in a solvent for the fluorination reaction, has been obtained, and this has been employed as a substrate for the fluorination reaction. And, the present invention has been accomplished wherein such a substrate is fluorinated in a liquid phase, and then the ester bond is splitted to obtain the desired fluorinated ketone (5). Further, it has been found that a process of recycling an acylfluoride compound (6) which is formed together with the fluorinated ketone (5) by this dissociation reaction, is an industrially useful process for producing a fluorinated ketone (5).

Namely, the present invention provides a process for producing a fluorinated ketone of the following formula (5), which comprises reacting a compound of the following formula (3) having a fluorine content of at least 30 mass %, with fluorine in a liquid phase to obtain a compound of the following formula (4), and then, subjecting the ester linkage of the compound of the formula (4) to a dissociation reaction:

  (3)

  (4)

  (5)

wherein each of $R^A$ and $R^{AF}$ which may be the same or different, is a monovalent organic group, provided that when $R^A$ and $R^{AF}$ are different, $R^{AF}$ is a monovalent organic group formed by fluorination of $R^A$, and each of $R^B$ and $R^{BF}$ which may be the same or different, is a monovalent organic group, provided that when $R^B$ and $R^{BF}$ are different, $R^{BF}$ is a monovalent organic group formed by fluorination of $R^B$, and at least one of $R^{AF}$ and $R^{BF}$ is a fluorinated monovalent organic group; or $R^A$ and $R^B$ may be bonded to each other to form a bivalent organic group, and in such a case, $R^{AF}$ and $R^{BF}$ are bonded to each other to form a bivalent organic group, the bivalent organic group formed by $R^{AF}$ and $R^{BF}$ is a fluorinated bivalent organic group, the bivalent organic group formed by $R^A$ and $R^B$ and the bivalent organic group formed by $R^{AF}$ and $R^{BF}$ may be the same or different, provided that when they are different, the bivalent organic group formed by $R^{AF}$ and $R^{BF}$ is a group formed by fluorination; and each of $R^C$ and $R^{CF}$ which may be the same or different, is a monovalent organic group, provided that when $R^C$ and $R^{CF}$ are different, $R^{CF}$ is a monovalent organic group formed by fluorination of $R^C$, and provided that at least one of $R^A$, $R^B$ and $R^C$ is a group having an atom or an atomic group which can be substituted by a fluorine atom, and at least one of $R^A$, $R^B$ and $R^C$ is a group having a fluorine atom.

Further, the present invention provides the above process wherein the compound of the formula (3) is a compound obtained by reacting a compound of the formula (1) and a compound of the formula (2):

$$HOCHR^A R^B \qquad (1)$$

$$R^C COX \qquad (2)$$

$$R^C COOCHR^A R^B \qquad (3)$$

wherein $R^A$, $R^B$ and $R^C$ are as defined above, and X is a halogen atom.

Further, the present invention provides the above process wherein a compound of the following formula (6) is obtained together with the fluorinated ketone of the formula (5) from the reaction product of the dissociation reaction of the ester linkage:

$$R^{CF} COF \qquad (6)$$

wherein $R^{CF}$ is as defined above.

Further, the present invention provides the process wherein the compound of the formula (2) which is reacted with the compound of the formula (1), is the compound of the formula (6) obtained by the above process.

BEST MODE FOR CARRYING OUT THE INVENTION

In the following description in this specification, a compound of the formula (3) will be referred to as a compound (3), and the same applies to compounds of other formulae.

In this specification, an organic group is a group which essentially contains carbon atoms, and it may be a saturated group or an unsaturated group. As an atom which can be substituted by a fluorine atom, a hydrogen atom bonded to carbon may be mentioned. As an atomic group which can be substituted by a fluorine atom, a carbon-carbon unsaturated double bond or a carbon-carbon unsaturated triple bond may, for example, be mentioned. For example, in a case where a carbon-carbon double bond is present in an organic group, fluorine will be added to the carbon-carbon double bond by a fluorination reaction in a liquid phase to form a carbon-carbon single bond. Further, in a case where a carbon-carbon triple bond is present in an organic group, fluorine will be added to the carbon-carbon triple bond by a fluorination reaction in a liquid phase to form a carbon-carbon single bond or a carbon-carbon double bond.

As the organic group, a hydrocarbon group, a hetero atom-containing hydrocarbon group, a halogenated hydrocarbon group or a halogenated (hetero atom-containing hydrocarbon) group is preferred. From the viewpoint of the solubility in the liquid phase to be employed for the fluorination reaction, the organic group is preferably a group having a carbon number of from 1 to 20, particularly preferably a group having a carbon number of from 1 to 10.

Here, the hydrocarbon group may be an aliphatic hydrocarbon group or an aromatic hydrocarbon group, and an aliphatic hydrocarbon group is preferred. Further, in the aliphatic hydrocarbon group, a single bond, a double bond or a triple bond may be present as the carbon-carbon bond. The aliphatic hydrocarbon group may be of a straight chain structure, a branched structure, a cyclic structure or a structure partially having a cyclic structure.

As the organic group, a saturated organic group is preferred. The saturated organic group is a group wherein the carbon-carbon bonds in the group are composed solely of single bonds. In such a group, an unsaturated bond (such as C=O or $SO_2$) other than a carbon-carbon unsaturated bond, may be present.

As the monovalent hydrocarbon group, a monovalent saturated hydrocarbon is preferred. As the monovalent saturated hydrocarbon group, an alkyl group may be mentioned, and its structure may be a straight chain structure, a branched structure, a cyclic structure, or a structure which is partially cyclic. As the bivalent saturated hydrocarbon group, an alkylene group may be mentioned, and its structure may be a straight chain structure, a branched structure, a cyclic structure or a structure having a cyclic portion.

The carbon number in the alkyl group or the alkylene group is preferably from 1 to 10. The alkyl group having a straight chain structure may, for example, be a methyl group, an ethyl group, a propyl group or a butyl group. The alkyl group having a branched structure may, for example, be an isopropyl group, an isobutyl group, a sec-butyl group or a tert-butyl group. The alkyl group having a cyclic structure may, for example, be a cycloalkyl group, a bicycloalkyl group or a group having an alicyclic spiro structure, and a 3- to 6-membered cycloalkyl group is preferred, such as a cyclopentyl group or a cyclohexyl group.

The alkyl group having a cyclic portion may be an alkyl group (of a straight chain structure or a branched structure) substituted by an alkyl group having the above-mentioned cyclic structure, or a group having a cyclic group portion of such an alkyl group further substituted by an alkyl group (of a straight chain structure or a branched structure), preferably a group having at least one hydrogen atom of an alkyl group substituted by a 3- to 6-membered cycloalkyl group, particularly preferably a cyclopentyl methyl group, a cyclohexyl ethyl group or an ethylcyclohexyl methyl group. The alkyl group having a cyclic portion may be an alkyl group having an aromatic ring (for example, an aralkyl group such as a benzyl group or a phenethyl group) or an alkyl group having a heterocyclic group (for example, a pyridylmethyl group or a furfuryl group).

Further, the alkylene group may be a group having one of the hydrogen atoms of the above alkyl group converted to a binding site, preferably an alkylene group having a straight chain structure or a branched structure.

The hetero atom-containing hydrocarbon group may be a group comprising a hetero atom such as an oxygen atom, a nitrogen atom or a sulfur atom, carbon atoms and hydrogen atoms. And, the hetero atom may be a hetero atom itself, or in the form of a hetero atom group wherein hetero atoms are bonded to one another or a hetero atom and other atoms are bonded. Each of such a hetero atom and a hetero atom group is preferably one which will not be changed by a thermal decomposition. The hetero atom may, for example, be an etheric oxygen atom (O in C—O—C), =O or ≡N, particularly preferably an etheric oxygen atom. The carbon number in the hetero atom-containing hydrocarbon group is preferably from 1 to 20. The hetero atom-containing hydrocarbon group is preferably a saturated group, particularly preferably a group having a bivalent hetero atom or a bivalent hetero atom group inserted between the carbon-carbon atoms of such a saturated hydrocarbon group, or a group having a hetero atom bonded to a carbon atom in such a saturated hydrocarbon group, or a group having a bivalent hetero atom or a bivalent hetero atom group bonded to a carbon atom at the bond terminal of such a saturated hydrocarbon group.

The hetero atom-containing hydrocarbon group is particularly preferably an etheric oxygen atom-containing compound from the viewpoint of usefulness of the compound. Particularly from the viewpoint of availability, production efficiency and usefulness of the product, the monovalent group is preferably an alkyl group containing an etheric oxygen atom (for example, an alkoxyalkyl group), and the bivalent group is preferably an alkylene group containing an etheric oxygen atom (for example, a polyoxyalkylene group). Further, the hetero atom-containing hydrocarbon group having a cyclic portion may, for example, be a group having a dioxolane skeleton.

The alkoxyalkyl group is preferably a group having one of hydrogen atoms present in the above alkyl group substituted by an alkoxy group. The carbon number of such an alkoxy group is preferably from 1 to 10. The alkoxyalkyl group may, for example, be an ethoxymethyl group, a 1-propoxyethyl group or a 2-propoxyethyl group.

The halogen atom in the halogenated group is a fluorine atom, a chlorine atom, a bromine atom or an iodine atom, preferably a fluorine atom, a chlorine atom or a bromine atom, particularly preferably a fluorine atom, or a fluorine atom and a chlorine atom, from the viewpoint of the usefulness of the compound.

In this specification, halogenated means that at least one hydrogen atom is substituted by a halogen atom. Partially halogenated means that some of hydrogen atoms are substituted by halogen atoms. Namely, in the partially halogenated group, a hydrogen atom is present. Perhalogenated means that all of hydrogen atoms are fluorinated. Namely, no hydrogen is present in a perhalogenated group. The meanings of terms such as halogenated, partially halogenated and perhalogenated are similar also in the meanings of terms such as fluoro, partially fluoro, partially chloro and perfluoro. Halogen atoms present in a halogenated group or a perhalogenated group may be of one type or two or more types.

A halogenated hydrocarbon group is a group having at least one hydrogen atom present in a hydrocarbon group substituted by a halogen atom. A hydrogen atom may or may not be present in the halogenated hydrocarbon group. The halogen atom in a halogenated hydrocarbon group is preferably a fluorine atom, a chlorine atom, or a fluorine atom and a chlorine atom. The partially halogenated hydrocarbon group is a group having some of hydrogen atoms present in a hydrocarbon group are substituted by halogen atoms. In the partially halogenated hydrocarbon group, a hydrogen atom is present. A perhalogenated hydrocarbon group is a group having all of hydrogen atoms present in a hydrocarbon group substituted by halogen atoms. No hydrogen atom is present in the perhalogenated hydrocarbon group.

The halogenated hydrocarbon group may be of a straight chain structure or a branched structure, and it may have a cyclic structure or a cyclic portion and is preferably a saturated group. Among halogenated hydrocarbon groups, a monovalent saturated group may, for example, be a fluoroalkyl group or a fluoro (partially chlorinated alkyl) group, and a bivalent saturated group may, for example, be a fluoroalkylene group or a fluoro partially chlorinated alkylene) group. The carbon number in the halogenated saturated hydrocarbon group is preferably from 1 to 20.

Among perhalogenated hydrocarbon groups, a monovalent saturated group is preferably a perfluoroalkyl group or a perfluoro (partially chlorinated alkyl) group (i.e. a group having all hydrogen atoms in a partially chlorinated alkyl group fluorinated), and a bivalent saturated group is preferably a perfluoroalkylene group or a perfluoro (partially chlorinated alkylene) group (i.e. a group having all hydrogen atoms in a partially chlorinated alkylene group fluorinated). Here, the perfluoro (partially chlorinated alkyl) group is the same as a perfluoroalkyl group, and a perfluoro (partially chlorinated alkylene) group is the same as a perfluoroalkylene group.

The halogenated (hetero atom-containing hydrocarbon) group may be of a straight chain structure or a branched structure and is preferably a fluoro (hetero atom-containing hydrocarbon) group or a fluoro (partially chlorinated (hetero atom-containing hydrocarbon)) group. The carbon number in the halogenated (hetero atom-containing saturated hydrocarbon) group is preferably from 1 to 20, and a saturated group is preferred.

The perhalogenated (hetero atom-containing monovalent hydrocarbon) group is preferably a perfluoro (hetero atom-containing monovalent hydrocarbon) group or a perfluoro (partially chlorinated (hetero atom-containing monovalent hydrocarbon)) group, particularly preferably a fluoro (hetero atom-containing alkyl) group or a fluoro (partially chlorinated (hetero atom-containing alkyl)) group, especially preferably a perfluoro (alkoxyl) group or a perfluoro (partially chlorinated (alkoxyl)) group. The perhalogenated (hetero atom-containing bivalent hydrocarbon) group is a group having one halogen atom in a perhalogenated (hetero atom-containing monovalent hydrocarbon) group converted to a binding site, and is preferably a perfluoro (polyoxyalkylene) group.

Examples of these groups will be specifically shown in the specific compounds which will be given hereinafter.

The compound (3) is preferably a compound wherein $R^A$ is a monovalent saturated hydrocarbon group, a partially halogenated monovalent hydrocarbon group, an etheric oxygen atom-containing monovalent saturated hydrocarbon group or a partially halogenated (etheric oxygen atom-containing monovalent hydrocarbon) group, $R^B$ is a monovalent saturated hydrocarbon group, a partially halogenated monovalent hydrocarbon group, an etheric oxygen atom-containing monovalent saturated hydrocarbon group or a partially halogenated (etheric oxygen atom-containing monovalent hydrocarbon) group, and $R^C$ is a group having all hydrogen atoms present in a group selected from a monovalent saturated hydrocarbon group, an etheric oxygen atom-containing monovalent hydrocarbon group and a partially halogenated (etheric oxygen atom-containing monovalent saturated hydrocarbon) group, substituted by fluorine atoms.

Otherwise, the compound (3) is preferably a compound wherein $R^A$ and $R^B$ are bonded to each other to form a bivalent saturated hydrocarbon group, a partially halogenated bivalent saturated hydrocarbon group, an etheric oxygen atom-containing bivalent saturated hydrocarbon group or a partially halogenated (etheric oxygen atom-containing bivalent saturated hydrocarbon) group, and $R^C$ is a group having all hydrogen atoms present in a group selected from a monovalent saturated hydrocarbon group, a partially halogenated monovalent saturated hydrocarbon group, an etheric oxygen atom-containing monovalent saturated hydrocarbon group, and a partially halogenated (etheric oxygen atom-containing monovalent hydrocarbon) group, substituted by fluorine atoms.

In the present invention, the fluorine content of the compound (3) (the fluorine content is a ratio of the mass of fluorine atoms to the molecular weight) is at least 30 mass %. Namely, the compound (3) is a compound containing a fluorine atom. Accordingly, at least one of $R^A$, $R^B$ and $R^C$ is a group having a fluorine atom. Each of $R^A$ and $R^B$ is preferably a group having a hydrogen atom, and $R^C$ is preferably a group having a fluorine atom (particularly preferably a perfluoro group).

The fluorine content is preferably from 30 to 86 mass %, particularly preferably from 30 to 76 mass %. If the fluorine content is too small, the solubility into the liquid phase tends to be extremely low, and the reaction system for the fluorination reaction tends to be heterogeneous, and in the continuous reaction, the compound (3) may not well be fed into the reaction system. The upper limit for the fluorine content is not particularly limited, but if it is too high, such a compound (3) tends to be hardly available, thus leading to a problem that the price is high and not economical.

Further, the molecular weight of the compound (3) is preferably from 200 to 1,000. With the molecular weight, an undesirable fluorination reaction in a gas phase can be prevented, and the fluorination reaction in the liquid phase can be carried out smoothly. If the molecular weight is too small, the compound (3) is likely to be readily vaporized, whereby it is likely that a decomposition reaction takes place in a gas phase during the fluorination reaction in the liquid phase. On the other hand, if the molecular weight is too large, purification of the compound (3) is likely to be difficult.

The following compounds may be mentioned as specific examples of the compound (3). However, in this specification, Cy represents a cyclohexyl group.

$CF_3CF_2CF_2OCF(CF_3)COOCH(CH_3)_2$,
$CF_3CF_2CF_2OCF(CF_3)COOCH(CH_3)CH_2CHClCH_2Cl$,
$CF_3CF_2CF_2OCF(CF_3)COOCH(CH_3)CH_2CH_3$,
$CF_3CF_2CF_2OCF(CF_3)COOCH(CH_3)CH_2CH_2CH_3$,
$CF_3CF_2CF_2OCF(CF_3)COOCy$,
$CF_3CF_2CF_2OCF(CF_3)COOCH(CH_3)CH_2CFClCF_2Cl$,
$CF_3CF_2CF_2OCF(CF_3)CF_2OCF(CF_3)COOCH(CH_3)_2$,

The compound (3) may be a commercially available compound. However, in the present invention, it is preferred to use a compound (3) obtained by reacting a compound (1) and a compound (2), since it is thereby possible to obtain the desired compound (3) within a wide range.

$HOCHR^AR^B$ (1)

$R^CCOX$ (2)

$R^CCOOCHR^AR^B$ (3)

wherein $R^A$, $R^B$ and $R^C$ are as defined above, and X is a halogen atom.

The compound (1) is a so-called secondary alcohol, and various compounds differing in the structure of $—CHR^AR^B$ can easily be obtained. Accordingly, a desired fluorinated ketone (5) can be produced by obtaining a compound (1) corresponding to the structure of the desired fluorinated ketone (5). As the compound (1), it is necessary only to obtain a compound (1) having a group ($R^A$) corresponding to $R^{AF}$ in the desired fluorinated ketone (5) and a group ($R^B$) corresponding to $R^{BF}$ therein. And, according to the reaction by the process of the present invention, a fluorinated ketone (5) which can hardly be obtained by conventional methods, can be produced. An example of such a fluorinated ketone (5) which can hardly be obtained by conventional methods, may be a compound wherein the structure of $R^{AF}$ or $R^{BF}$ is complex, or a fluorinated product corresponding to a low molecular weight compound from which various types of by-products will be formed by a fluorination reaction. As an example of the latter, a fluorinated ketone (5) corresponding to a compound (1) having a molecular weight of at most 200, particularly one corresponding to a compound (1) having a molecular weight of from 50 to 200, may be mentioned.

The following compounds may be mentioned as specific examples of the compound (1).

$(CH_3)_2CHOH$,
$CH_3CH_2CH(CH_3)OH$,
$CH_2=CHCH(CH_3)OH$,
$CH_3CH_2CH_2CH(CH_3)OH$,
$CH_2ClCHClCH_2CH(CH_3)OH$,
$CF_2ClCFClCH_2CH(CH_3)OH$,
CyOH,

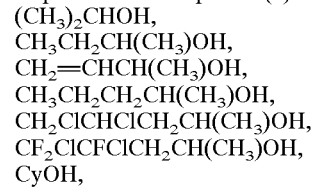

$R^C$ in the compound (2) to be reacted with the compound (1) is selected so that the fluorine content of the compound (3) will be at least 30 mass %. The carbon number of $R^C$ is preferably from 1 to 20, particularly preferably from 1 to 10. The carbon number of $R^C$ is particularly preferably from 2 to 10, whereby the after-mentioned continuous process can easily be carried out, and the molecular weight of the compound (3) can be made high.

The following compounds may be mentioned as specific examples of the compound (2).

$CF_3CF_2COF$,
$CF_3CF_2CF_2OCF(CF_3)COF$,
$CF_3CF_2CF_2OCF(CF_3)CF_2OCF(CF_3)COF$.

The compound (2) may be a commercial product or a compound (6) which is the product by the process of the present invention. A compound corresponding to the compound (2) wherein X is a fluorine atom, is one embodiment of the compound (6). As the compound (1), an aliphatic secondary alcohol containing no fluorine atom is readily available, and accordingly, $R^C$ in the compound (6) is preferably a group containing a fluorine atom. Especially in a case where a continuous process is carried out by employing the compound (6) as the compound (2) to be reacted with the compound (1), it is preferred that $R^C$ and $R^{CF}$ are the same group, particularly a perfluoro monovalent organic group. Preferred embodiments of such a perfluoro monovalent organic group are as described above.

The reaction of the compound (1) and the compound (2) can be carried out by applying a reaction method and conditions of a known esterification reaction. The reaction may be carried out in the presence of a solvent (hereinafter referred to as the solvent 1), but from the viewpoint of the volume efficiency, it is preferred to carry out the reaction in the absence of the solvent 1. In a case where the solvent 1 is employed, dichloromethane, chloroform, triethylamine or a mixed solvent of triethylamine and tetrahydrofuran, is preferred. The solvent 1 is used preferably in an amount of from 50 to 500 mass %, based on the total amount of the compound (1) and the compound (2).

In the reaction of the compound (1) and the compound (2), HF will be generated, and as a scavenger for HF, an alkali metal fluoride (NaF or KF is preferred) or a trialkylamine may be present in the reaction system. It is better to use the scavenger for HF, in a case where the compound (1) or the compound (2) is a compound which is instable to an acid. On the other hand, in a case where the scavenger for HF is not used, it is preferred that HF is discharged from the reaction system together with a nitrogen stream. In a case where an alkali metal fluoride is employed, its amount is preferably from 1 to 10 times by mol to the compound (2).

The temperature of the reaction of the compound (1) and the compound (2) is, in a usual case, preferably at least $-50°$ C. and at most $+100°$ C. or at most the boiling point of the solvent. Further, the reaction time for the reaction may optionally be changed depending upon the feeding rates of the raw materials and the amounts of the compounds to be used for the reaction. The pressure for the reaction (gauge pressure, the same applies hereinafter) is preferably from 0 to 2 MPa.

The ratio in amount of the compound (1) and the compound (2) is preferably such that the amount of the compound (2) to the compound (1) is from 0.5 to 5 times by mol, particularly preferably from 1 to 2 times by mol.

The crude product containing the compound (3) formed by the reaction of the compound (1) and the compound (2), may be purified depending upon the particular purpose, or may be used as it is, for the next reaction or the like. However, from the viewpoint of carrying out the fluorination reaction in the next step constantly, it is advisable that the crude product is purified to separate the compound (3).

The method for purifying the crude product may, for example, be a method of distilling the crude product as it is, a method of treating the crude product with e.g. a dilute alkaline aqueous solution, followed by liquid separation, a method of extracting the crude product with a suitable organic solvent, followed by distillation, or silica gel column chromatography.

In the present invention, the compound (3) is reacted with fluorine in a liquid phase to obtain a compound (4). In the present invention, the fluorination reaction means a reaction wherein at least one fluorine atom will be bonded to the molecule of the compound (3).

In the compound (4), $R^{AF}$ is a group corresponding to $R^A$, $R^{BF}$ is a group corresponding to $R^B$, and $R^{CF}$ is a group corresponding to $R^C$. In these groups, there will be no change in the arrangement of carbon atoms as between before and after the fluorination reaction, and a compound corresponding to the compound (3) will be obtained. However, in a case where a carbon-carbon unsaturated bond is present in the compound (3), the bond state may be changed by addition of fluorine atoms to at least one such unsaturated bond, as mentioned above.

In the present invention, the fluorination in the liquid phase is preferably carried out by a method wherein fluorine gas is introduced into a solvent for fluorination.

The fluorine gas may be used as it is, or fluorine gas diluted with an inert gas, may be employed. The inert gas is preferably nitrogen gas or helium gas, and nitrogen gas is particularly preferred from the economical reason. The amount of fluorine gas in nitrogen gas is not particularly limited and is preferably at least 10% from the viewpoint of efficiency, particularly preferably at least 20%.

As the liquid phase, it is preferred to employ a solvent (hereinafter referred to as the solvent 2) capable of dissolving fluorine ($F_2$). The solvent 2 is preferably a solvent which contains no C—H bond and which essentially contains a C—F bond. Further, a perfluoroalkane or an organic solvent having a known organic solvent containing at least one atom selected from a chlorine atom, a hydrogen atom and an oxygen atom in its structure, perfluorinated, is preferred. Further, as the solvent 2, it is preferred to employ a solvent in which the solubility of the compound (3) is high, particularly preferably a solvent which is capable of dissolving at least 1 mass % of the compound (3), especially preferably a solvent which is capable of dissolving at least 5 mass % thereof.

As an example of the solvent 2, a perfluoroalkane (such as FC-72®), a perfluoroether (such as FC-75 or FC-77®), a perfluoropolyether (such as KRYTOX®, FOMBLIN®, GALDEN® or DEMNUM®, tradename), a chlorofluorocarbon (FLONRUBE®, tradename), a chlorofluoropolyether, a perfluoroalkylamine (such as a perfluorotrialkylamine) or an inert fluid (FLUORINERT®, tradename) may, for example, be mentioned.

Further, as the solvent 2, it is possible to employ at least one member selected from a compound (2), a compound (4), a fluorinated ketone (5) and an after-mentioned compound (6), having a function as a solvent. Especially when the compound (4), the fluorinated ketone (5) or the compound (6) is used, there is a merit such that post treatment after the reaction will be easy.

The solvent 2 is preferably used in an amount of at least 5 times by mass, particularly preferably from 10 to 100 times by mass, to the compound (3).

A batch system or a continuous system is preferred as the reaction system for the fluorination reaction. Further, from the viewpoint of the reaction yield and the selectivity, it is preferred to employ a fluorination method 2, which will be described below. Further, fluorine gas may be used as diluted with an inert gas such as nitrogen gas in either case where the reaction is carried out in a batch system or where the reaction is carried out in a continuous system.

Fluorination method 1: Into a reactor, the compound (3) and the solvent 2 are charged, and stirring is initiated. Then, at a prescribed reaction temperature under a prescribed reaction pressure, the reaction is carried out while continuously supplying the fluorine gas into the liquid phase in the reactor.

Fluorination method 2: Into a reactor, the solvent 2 is charged, and stirring is initiated. Then, at a prescribed reaction temperature under a prescribed reaction pressure, the compound (3) and the fluorine gas are continuously and simultaneously supplied in a prescribed molar ratio to the liquid phase in the reactor. In the method 2, when the compound (3) is supplied, it may or may not be diluted with the solvent 2. Further, in the method 2, when the compound (3) is diluted with a solvent, the amount of the solvent 2 to the compound (3) is adjusted preferably to at least 5 times by mass, particularly preferably at least 10 times by mass.

With respect to the amount of fluorine to be used for the fluorination reaction, in a case where the reaction is carried out in a batch system, it is preferred to charge fluorine gas so that the amount of fluorine is always in an excess equivalent to hydrogen atoms in the compound (3), and from the viewpoint of the selectivity, it is particularly preferred to use fluorine so that the amount will be at least 1.5 times by equivalent (i.e. at least 1.5 times by mol). Further, in a case where the reaction is carried out in a continuous system, it is preferred to continuously supply fluorine so that the amount of fluorine will be in an excess equivalent to hydrogen atom in the compound (3), and from the viewpoint of selectivity, it is particularly preferred to continuously supply fluorine gas so that it will be at least 1.5 times by equivalent to the compound (3). Further, the amount of fluorine is preferably maintained to be always in an excess equivalent from the initiation to the termination of the reaction.

The reaction temperature for the fluorination reaction by the fluorination method 1 is usually preferably at least −60° C. and at most the boiling point of the compound (3), and from the viewpoint of the reaction yield, the selectivity and the industrial efficiency, it is particularly preferably from −50° C. to +100° C., especially preferably from −20° C. to +50° C. The reaction pressure for the fluorination reaction is not particularly limited, a pressure of from 0 to 2 MPa is particularly preferred from the viewpoint of the reaction yield, the selectivity and the industrial efficiency.

Further, in order to let the fluorination method 1 proceed efficiently, it is preferred to add a C—H bond-containing compound into the reaction system or to carry out ultraviolet irradiation. For example, in a batch system reaction, it is preferred to add a C—H bond-containing compound to the reaction system at a later stage of the fluorinated reaction, or to carry out ultraviolet irradiation at a second step in the continuous system. It is thereby possible to efficiently fluorinate the compound (3) present in the reaction system, whereby the conversion can remarkably be improved. The time for ultraviolet irradiation is preferably from 0.1 to 3 hours.

The C—H bond-containing compound is preferably an organic compound other than the compound (3), particularly preferably an aromatic hydrocarbon, especially preferably benzene, toluene or the like. The amount of the C—H bond-containing compound is preferably from 0.1 to 10 mol %, particularly preferably from 0.1 to 5 mol %, to hydrogen atoms in the compound (3).

It is preferred to add the C—H bond-containing compound in a state where fluorine gas is present in the reaction system. Further, in a case where the C—H bond-containing compound is added, it is preferred to pressurize the reaction system. The pressure for pressurizing is preferably from 0.01 to 5 MPa.

The compound (4) is a compound having the compound (3) fluorinated, and it is preferably a perfluorinated compound.

Namely, $R^{AF}$ in the compound (4) is the same group as $R^A$ or a monovalent organic group formed by fluorination of $R^A$ (i.e. a fluoro monovalent organic group).

Namely, in a case where $R^A$ does not have an atom or an atomic group which can be substituted by a fluorine atom or is not fluorinated, $R^{AF}$ is the same group as $R^A$, and in a case where $R^A$ has an atom or an atomic group which can be substituted by a fluorine atom, or is fluorinated, $R^{AF}$ is a group different from $R^A$. Likewise, $R^{BF}$ is the same group as $R^B$ or a monovalent organic group formed by fluorination of $R^B$. Otherwise, in a case where $R^A$ and $R^B$ are bonded to each other to form a bivalent organic group, the bivalent organic group formed by $R^{AF}$ and $R^{BF}$, is a fluorinated bivalent organic group. And, in a case where the bivalent organic group formed by $R^A$ and $R^B$, is not fluorinated, such a bivalent organic group is the same group as the bivalent organic group formed by $R^{AF}$ and $R^{BF}$, and in a case where the bivalent organic group formed by $R^A$ and $R^B$, is fluorinated, such a bivalent organic group is a group different from the bivalent organic group formed by $R^{AF}$ and $R^{BF}$. Further, the desired compound of the present invention is a fluorinated compound, whereby at least one of $R^{AF}$ and $R^{BF}$, or the bivalent organic group formed by $R^{AF}$ and $R^{BF}$, is a group containing a fluorine atom.

As the compound (3) being a substrate for the fluorination reaction, a compound (3) wherein $R^A$ and $R^B$ are groups containing hydrogen atoms, is readily available. Accordingly, $R^{AF}$ and $R^{BF}$ in the compound (4) are preferably groups formed by fluorination of $R^A$ and $R^B$, respectively, (i.e. fluoro groups), particularly preferably groups formed by perfluorination (i.e. perfluoro groups).

Namely, $R^{AF}$ is preferably a group having at least one hydrogen atom (preferably all hydrogen atoms) present in a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group, substituted by a fluorine atom. $R^{BF}$ is preferably a group having at least one hydrogen atom (preferably all hydrogen atoms) present in a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group, substituted by a fluorine atom.

Otherwise, preferred is a group having at least one hydrogen atom (preferably all hydrogen atoms) in a bivalent saturated hydrocarbon group, a partially halogenated bivalent saturated hydrocarbon group, an etheric oxygen atom-containing bivalent saturated hydrocarbon group or a partially halogenated (etheric oxygen atom-containing bivalent saturated hydrocarbon) group, formed by bonding of $R^{AF}$ and $R^{BF}$ to each other, substituted by a fluorine atom.

$R^{CF}$ is preferably a group having all hydrogen atoms present in a group selected from a monovalent saturated hydrocarbon group, a partially halogenated bivalent saturated hydrocarbon group, an etheric oxygen atom-containing monovalent saturated hydrocarbon group and a partially halogenated (etheric oxygen atom-containing monovalent saturated hydrocarbon) group, substituted by fluorine atoms.

The following compounds may be mentioned as specific examples of the compound (4). However, in the present specification, $Cy^F$ represents a perfluorocyclohexyl group.

$CF_3CF_2CF_2OCF(CF_3)COOCF(CF_3)_2$,
$CF_3CF_2CF_2OCF(CF_3)COOCF(CF_3)CF_2CFClCF_2Cl$,
$CF_3CF_2CF_2OCF(CF_3)COOCF(CF_3)CF_2CF_3$,
$CF_3CF_2CF_2OCF(CF_3)COOCF(CF_3)CF_2CF_2CF_3$,
$CF_3CF_2CF_2OCF(CF_3)COOCy^F$,
$CF_3CF_2CF_2OCF(CF_3)CF_2OCF(CF_3)COOCF(CF_3)_{20}$

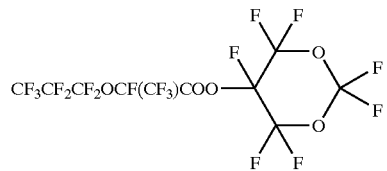

In the fluorination reaction, HF will be formed as a by-product when a reaction takes place to substitute a hydrogen atom by a fluorine atom. To remove the by-product HF, it is preferred to let a scavenger for HF be present in the reaction system or to let a HF scavenger and the outlet gas contact each other at the gas outlet of the reactor. As such a HF scavenger, the same one as described above can be employed, and NaF is preferred.

In a case where the HF scavenger is permitted to be present in the reaction system, its amount is preferably from 1 to 20 times by mol, more preferably from 1 to 5 times by mol, to the total amount of hydrogen atoms present in the compound (3). In a case where the HF scavenger is permitted to be present at the gas outlet of the reactor, (a) a cooler maintained preferably at a temperature of from 10° C. to room temperature, particularly preferably at about 20° C.), (b) a layer packed with NaF pellets and (c) a cooler (maintained preferably at from −78° C. to +10° C., more preferably from −30° C. to 0° C.) are preferably set in series in the order of (a)-(b)-(c). Further, a liquid-returning line may be installed to return the condensed liquid from the cooler of (c) to the reactor.

The crude product containing the compound (4) obtained by the fluorination reaction, may be used as it is for the next step, or may be purified to one having high purity. The purification method may, for example, be a method of distilling the crude product as it is under normal pressure or reduced pressure.

In the present invention, the ester linkage of the compound (4) is further subjected to a dissociation reaction to obtain a fluorinated ketone (5). The reaction for dissociating the ester linkage of the compound (4) is preferably carried out by heating to cleave the ester linkage, or to cleave the ester linkage in the presence of a nucleophilic agent or in the presence of an electrophilic agent.

In the case where the ester linkage is cleaved by heating (hereinafter referred to as pyrolysis), it is preferred to select the type of the pyrolytic reaction depending upon the boiling point and the stability of the compound (4). For example, in a case where a volatile compound (4) is subjected to pyrolysis, a gas phase pyrolysis method may be employed in which pyrolysis is continuously carried out in a gas phase, and the outlet gas containing the obtained fluorinated ketone (5) is condensed and recovered. The gas phase pyrolysis method is advantageous as an industrial production method, and it is particularly preferred when a catalyst is used, since separation of the catalyst and the solvent will be unnecessary.

The reaction temperature for the gas phase pyrolysis method is preferably from 50 to 350° C., particularly preferably from 50 to 300° C., especially preferably from 150 to 250° C. Further, an inert gas which will not directly be interact in the reaction, may be present in the reaction system. Such an inert gas may, for example, be nitrogen gas or carbon dioxide gas. The inert gas is added preferably in an amount of from about 0.01 to 50 vol % based on the compound (4). If the amount of the inert gas is large, the recovered amount of the product is likely to decrease.

Further, in the gas phase pyrolysis method, it is preferred to employ a tubular type reactor. When the tubular type reactor is employed, the residence time is preferably from about 0.1 second to 10 minutes on a space velocity basis. The pressure for the reaction is not particularly limited. Further, in a case when the compound (4) is a high boiling point compound, it is preferred to carry out the reaction under reduced pressure. Especially when the compound (4) is a low boiling point compound, it is preferred to carry out the reaction under an elevated pressure, since the decomposition of the product will thereby be suppressed, and the conversion will be improved.

When the gas phase reaction is carried out by means of the tubular type reactor, it is preferred to pack glass, an alkali metal salt, an alkaline earth metal salt or activated carbon in the reactor for the purpose of accelerating the reaction.

As the alkali metal salt or the alkaline earth metal salt, a carbonate or a fluoride is preferred. The alkali metal salt may, for example, be sodium carbonate, sodium fluoride, potassium fluoride, potassium carbonate or lithium carbonate. The alkaline earth metal salt may, for example, be calcium carbonate, calcium fluoride or magnesium carbonate. The glass may be common soda glass, and glass beads having flowability improved in the form of beads, are particularly preferred. Among them, an alkali metal salt, particularly an alkali metal fluoride, especially potassium fluoride, is particularly preferred in that the yield in the dissociation reaction is high, the reaction can be carried out even at a low reaction temperature, the reaction can be efficiently carried out even with a small amount of potassium fluoride, or the durability of the catalyst is high. Further, the alkali metal salt may be supported on a support. The support may, for example, be activated carbon, activated aluminum, zirconia or different types of alkali metals. Further, when glass, an alkali metal salt or an alkaline earth metal salt is to be packed in the reactor, it is particularly preferred to employ glass beads, light ash of sodium carbonate, etc., which have a particle size of from about 100 to 250 μm, whereby a fluidized bed type reaction system can be employed.

In the gas phase reaction, it is preferred to carry out the reaction in the presence of an inert gas which will not be directly interact in the pyrolytic reaction, for the purpose of accelerating vaporization of the compound (4). Such an inert gas may, for example, be nitrogen gas, carbon dioxide gas, helium gas or argon gas. The amount of the inert gas is preferably from about 0.01 to 50 vol %, based on the compound (4). If the amount of the inert gas is too large, the recovery rate of the product is likely to be low, such being undesirable.

On the other hand, in a case where the compound (4) is a hardly volatile compound, it is preferred to employ a liquid phase pyrolysis method wherein it is heated in the form of a liquid in the reactor. The pressure for the reaction in this case is not particularly limited. In a usual case, the product containing the fluorinated ketone (5) has a lower boiling point than the compound (4), and it is preferred to carry out the reaction while distilling by means of a reaction apparatus equipped with a distillation column, and to vaporize and continuously withdraw the product. Otherwise, a method may be employed wherein after completion of the heating, the product is withdrawn all at once from the reactor. The reaction temperature for this liquid phase pyrolysis method is preferably from 50 to 300° C., particularly preferably from 100 to 250° C.

The pyrolysis by the liquid phase pyrolysis method may be carried out without any solvent or in the presence of a solvent (hereinafter referred to as the solvent 3). However, it is preferred to carry out the reaction without any solvent, from the viewpoint of the volume efficiency or suppression of by-products. The solvent 3 is not particularly limited so long as it does not react with the compound (4), has compatibility with the compound (4) and does not react with the resulting fluorinated ketone (5) and the after-mentioned compound (6). Further, the solvent 3 is preferably selected to be one which is readily separable at the time of purification of the fluorinated ketone (5) or at the time of purification of the compound (6). As specific examples of the solvent 3, inert solvents such as perfluorotrialkylamine and perfluoronaphthalene, and a high boiling point chlorotrifluoroethylene oligomer (such as FLONRUBE®, tradename) among chlorofluorocarbons, are preferred. The amount of the solvent 3 is preferably from 10 to 1,000 mass %, based on the compound (4).

Further, in a case where the ester linkage is cleaved by a method of reacting the compound (4) with a nucleophilic agent or an electrophilic agent in a liquid phase, such a reaction may be carried out without any solvent or in the presence of a solvent (hereinafter referred to as the solvent 4). However, it is preferred to carry out the reaction without any solvent, from the viewpoint of the volume efficiency or suppression of by-products. The solvent 4 may be the same as the solvent 3. The nucleophilic agent is preferably a fluorine anion (F−), particularly preferably a fluorine anion derived from a fluoride of an alkali metal. As the fluoride of an alkali metal, NaF, NaHF$_2$, KF or CsF is preferred. Among them, NaF is particularly preferred from the viewpoint of the economical efficiency.

In a case where a nucleophilic agent (such as F−) is employed, F− is nucleophilically added to a carbonyl group present in the ester linkage of the compound (4), whereby $R^{AF}R^{BF}CFO^-$ will be eliminated, and an acid fluoride (compound (6)) will be formed at the same time. From $R^{AF}R^{BF}CFO^-$, F− is further eliminated to form a ketone (a fluorinated ketone (5)). However, depending upon the conditions for the pyrolytic reaction, the compound (6) may further be decomposed to form other compounds (for example, the after-mentioned unsaturated compounds). The eliminated F− will likewise react with another molecule of the compound (4). Accordingly, the nucleophilic agent to be used at the initial stage of the reaction may be in a catalytic amount or in excess. Namely, the amount of the nucleophilic agent such as F− is preferably from 1 to 500 mol %, particularly preferably from 10 to 100 mol %, especially preferably from 5 to 50 mol %, based on the compound (4). The reaction temperature is preferably from −30° C. to the boiling point of the solvent or the compound (4), particularly preferably from −20° C. to 250° C. This method is preferably carried out also in a reaction distillation system.

In the reaction product of the ester dissociation reaction of the compound (4), the fluorinated ketone (5) is contained. Further, under the usual condition, the compound (6) will be contained together with the fluorinated ketone (5).

In the process of the present invention, the fluorinated ketone (5) will be a desired compound, or the compound (6) as well as the fluorinated ketone (5) will be a desired compound. The fluorinated ketone (5) is by itself useful as a ketone type solvent containing a fluorine atom, and it is a useful intermediate which can be converted to other useful compounds.

The following compounds may be mentioned as specific examples of the fluorinated ketone (5).

(CF$_3$)$_2$CO,
CF$_3$CF$_2$COCF$_3$,
CF$_3$CF$_2$CF$_2$COCF$_3$,
CF$_2$ClCFClCF$_2$COCF$_3$,

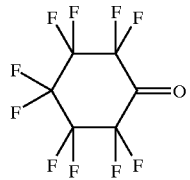
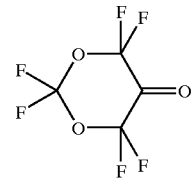

In a case where not only the fluorinated ketone (5) but also the compound (6) is contained in the reaction product of the ester dissociation reaction, it is possible to obtain the compound (6) together with the fluorinated ketone (5) from the reaction product and to use the compound (6) for other applications. For example, in the case of the following compound (6a) wherein $R^{CF}$— in the compound (6) is $R^{F1}R^1C(CF_3)$—, or the following compound (6b) wherein $R^{CF}$— is $R^{F2}R^2CFCF_2$—, these compounds may be pyrolysed to obtain the following compound (7a) or the following compound (7b), having a polymerizable unsaturated group introduced at a molecular terminal. Such a compound is useful as a monomer for a fluorine resin.

$R^{F1}CR^1(CF_3)COF$ (6a) ⟶ $R^{F1}R^1C=CF_2$ (7a)

$R^{F2}R^2CFCF_2COF$ (6b) ⟶ $R^{F2}R^2C=CF_2$ (7b)

$CF_3CF_2CF_2OCF(CF_3)COF$ ⟶ $CF_3CF_2CF_2OCF=CF_2$

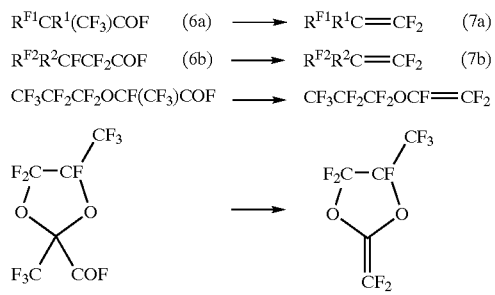

The following reactions may be exemplified as specific examples of the above reactions.

Further, when the compound (6) is used as the compound (2) to be reacted with the compound (1), the fluorinated ketone (5) can be continuously produced.

Namely, the fluorinated ketone (5) can be continuously produced by reacting the compound (1) with the compound (2) to obtain the compound (3), fluorinating the compound (3) in a liquid phase to obtain the compound (4), then dissociating the ester linkage of the compound (4) to obtain the fluorinated ketone (5) and the compound (6) and using a part or all of the compound (6) as the compound to be reacted with the compound (1).

According to the process of the present invention, various desired fluorinated ketones can be produced by using compounds (3) which are raw materials available at low costs. And, according to the process of the present invention, from such a raw material compound, the fluorinated ketone (5) and the compound (6) can be produced in high yield by a short process.

EXAMPLES

Now, the present invention will be described in detail with reference to Examples, but the present invention is not thereby limited. In the following, gas chromatography will be referred to as GC, and gas chromatography mass spectrometry will be referred to as GC-MS. Further, the purity determined by the peak area ratio of GC will be referred to as GC purity, and the corresponding yield will be referred to as GC yield. The yield determined from the peak area ratio of the NMR spectrum will be referred to as NMR yield. Further, tetramethylsilane will be referred to as TMS, and CCl$_2$FCClF$_2$ will be referred to as R-113. Further, the NMR spectrum data are shown within an apparent chemical shift range. The standard value of standard substance CDCl$_3$ in the $^{13}$C-NMR was 76.9 ppm. In the quantitative analysis by $^{19}$F-NMR, C$_6$F$_6$ was used as the internal standard.

Example 1

Example 1-1

Preparation Example for (CH$_3$)$_2$CHOCOCF(CF$_3$)OCF$_2$CF$_2$CF$_3$ (CH$_3$)$_2$CHOH (7.0 g) was put into a flask and stirred while bubbling nitrogen gas. FCOCF(CF$_3$)OCF$_2$CF$_2$CF$_3$ (45.5 g) was dropwise added over a period of 30 minutes, while maintaining the internal temperature at from 25 to 30° C. After completion of the dropwise addition, stirring was continued at room temperature for one hour, and a saturated sodium hydrogencarbonate aqueous solution (50 ml) was added at an internal temperature of at most 15° C.

The crude liquid was recovered as a lower layer by phase separation. Further, the lower layer was washed twice with water (50 ml), dried over magnesium sulfate and then filtered to obtain a crude liquid. By distillation under reduced pressure, 24.9 g of $(CH_3)_2CHOCOCF(CF_3)OCF_2CF_2CF_3$ was obtained as a fraction of from 67 to 68° C./10.7 kPa (absolute pressure). The purity by GC was 99%. The NMR spectrum data are as follows.

$^1$H-NMR (300.4 MHz, solvent: $CDCl_3$, standard: TMS) δ (ppm): 1.33 (d, J=6.0 Hz, 6H), 5.17 to 5.29 (m, 1H).

$^{19}$F-NMR (376.2 MHz, solvent: $CDCl_3$, standard: $CFCl_3$) δ (ppm): −79.6 (1F), −81.4 (3F), −82.3 (3F), −86.5 (1F), −129.6 (2F), −131.6 (1F).

Example 1-2

Preparation Example for $(CF_3)_2CFOCOCF(CF_3)OCF_2CF_2CF_3$

Into a 500 ml autoclave made of nickel, R-113 (312 g) was put, stirred and maintained at 25° C. At the gas outlet of the autoclave, a cooler maintained at −15° C. was installed. After supplying nitrogen gas for 1.0 hour, fluorine gas diluted to 20% with nitrogen gas (hereinafter referred to as 20% diluted fluorine gas) was supplied at a flow rate of 6.17 l/hr for one hour, and the internal pressure of the reactor was maintained at 0.15 MPa. Then, while maintaining the internal pressure of the reactor at 0.15 MPa by supplying 20% diluted fluorine gas at the same flow rate, a solution obtained by dissolving $(CH_3)_2CHOCOCF(CF_3)OCF_2CF_2CF_3$ (4.99 g) obtained by Example 1-1 in R-113 (100 g), was injected over a period of 5.3 hours.

Then, while maintaining the internal pressure of the reactor at 0.15 MPa by supplying 20% diluted fluorine gas at the same flow rate, a R-113 solution having a benzene concentration of 0.01 g/ml was injected in an amount of 9 ml while raising the temperature from 25° C. to 40° C., and the benzene inlet of the autoclave was closed and stirring was continued for 0.5 hour. Then, while maintaining the pressure of the reactor at 0.15 MPa by supplying 20% diluted fluorine gas at the same flow rate and maintaining the internal temperature of the reactor at 40° C., the above benzene solution was injected in an amount of 6 ml, whereupon the benzene inlet of the autoclave was closed, and stirring was continued for 0.5 hour.

Further, the same operation was repeated once. The total amount of benzene injected was 0.219 g, and the total amount of R-113 injected was 21 ml. Further, nitrogen was supplied for 1.5 hours. The product was quantified by $^{19}$F-NMR, whereby the yield of the above identified compound to $(CH_3)_2CHOCOCF(CF_3)OCF_2CF_2CF_3$, was 48.1%, and the yield of $(CF_3)_2CHOCOCF(CF_3)OCF_2CF_2CF_3$ to $(CH_3)_2CHOCOCF(CF_3)OCF_2CF_2CF_3$, was 19.1%.

$(CF_3)_2CFOCOCF(CF_3)OCF_2CF_2CF_3$: $^{19}$F-NMR (376.0 MHz, solvent: $CDCl_3$, standard: $CFCl_3$) δ (ppm): −79.4 (3F), −79.6 (3F), −79.9 (1F), −82.1 (3F), −82.2 (3F), −87.7 (1F), −130.4 (2F), −132.1 (1F), −143.4 (1F).

$(CF_3)_2CHOCOCF(CF_3)OCF_2CF_2CF_3$: $^{19}$F-NMR (376.0 MHz, solvent: $CDCl_3$, standard: $CFCl_3$) δ (ppm): −74.0 (3F), −74.1 (3F), −79.9 (IF), −82.3 (3F), −82.5 (3F), −87.7 (1F), −130.4 (2F), −132.6 (1F). $^1$H-NMR (399.0 MHz, solvent: $CDCl_3$, standard: TMS) δ (ppm): 5.80 (m, 1H).

Example 1-3

Preparation Example for $(CF_3)_2CO$ 2.1 g of a mixture of $(CF_3)_2CFOCOCF(CF_3)OCF_2CF_2CF_3$ and $(CF_3)_2CHOCOCF(CF_3)OCF_2CF_2CF_3$ obtained in Example 1-2, was charged into a flask together with 0.02 g of NaF powder and heated at 120° C. for 10 hours in an oil bath, while stirring vigorously. At an upper portion of the flask, a reflux condenser having the temperature adjusted at 20° C. and a gas bag were installed in series. After cooling, 1.5 g of a liquid sample and 0.4 g of a gas sample were recovered. The gas sample and the liquid sample were respectively analyzed by GC-MS, whereby from the gas sample, the above-identified compound was confirmed to be the main product, and from the liquid sample, $FCOCF(CF_3)OCF_2CF_2CF_3$ was confirmed to be the main product. The yield of the above-identified compound to $(CF_3)_2CFOCOCF(CF_3)OCF_2CF_2CF_3$, was 71.2%, as calculated by GC. Further, from the liquid sample, $FCOCF(CF_3)OCF_2CF_2CF_3$ (0.7 g) was obtained.

Example 1-4

Using $FCOCF(CF_3)OCF_2CF_2CF_3$ (0.7 g) obtained in Example 1-3, the reactions were carried out in the same manner as Example 1-1 to Example 1-3 to obtain $(CF_3)_2CO$ Example 2

Preparation Example for $CF_2ClCFClCF_2COCF_3$

Example 2-1

Preparation Example for $CH_2=CHCH_2CH(CH_3)OCOCF(CF_3)OCF_2CF_2CF_3$ $CH_2=CHCH_2CH(CH_3)OH$ (13.08 kg) was put into a reactor and stirred while bubbling nitrogen gas. $FCOCF(CF_3)OCF_2CF_2CF_3$ (54.29 kg) was charged over a period of 5 hours, while maintaining the internal temperature at from 25 to 30° C. After completion of the charging, the stirring was carried out for 70 hours at an internal temperature of from 30 to 50° C., while bubbling nitrogen gas.

The obtained crude liquid (58.32 kg) was used for the next step without being purified. The purity by GC was 96.6%. The NMR spectrum data were as follows.

$^1$H-NMR (300.4 MHz, solvent: $CDCl_3$, standard: TMS) δ (ppm): 1.32 (d, J=6.0 Hz, 3H), 2.30 to 2.50 (m, 2H), 5.07 to 5.21 (m, 3H), 5.61 to 5.76 (m, 1H).

$^{19}$F-NMR (282.7 MHz, solvent: $CDCl_3$, standard: $CFCl_3$) δ (ppm): −79.6 (1F), −81.3 (3F), −82.0 (3F), −86.3 (1F), −129.4 (2F), −131.5 (1F).

Example 2-2

Preparation Example for $CF_3CF_2CF_2OCF(CF_3)COOCH(CH_3)CH_2CHClCH_2Cl$ by Chlorination Reaction Into a 5 l flask equipped with a reflux condenser adjusted at 20° C., the compound (5,000 g) obtained in Example 2-1 was charged, and the reactor was cooled to −30° C. Then, $Cl_2$ was continuously supplied for bubbling in the reaction solution, and the supply rate of $Cl_2$ was controlled so that the temperature rise by the heat of the reaction would be at most 10° C. When the reaction proceeded and no more heat generation was observed, the reaction was terminated. After termination of the reaction, the temperature of the reactor was raised to room temperature and nitrogen gas was bubbled in the reaction solution for 24 hours to purge and remove excess $Cl_2$ to obtain a crude liquid (5,900 g). As a result of the GC analysis, the above-identified compound was found to have formed in a yield of 95%.

Example 2-3

Preparation Example for $CF_2ClCFClCF_2CF(CF_3)$ $OCOCF(CF_3)OCF_2CF_2CF_3$ by Fluorination Reaction Into a 500 ml autoclave made of nickel, R-113 (468 g) was put, stirred and maintained at 25° C. At the gas outlet of the autoclave, a cooler maintained at 5° C. and a layer packed with NaF pellets were installed in series. After supplying nitrogen gas for one hour at room temperature, the internal pressure of the autoclave was maintained at 0.15 MPa, while supplying fluorine gas diluted to 20% with nitrogen gas for one hour at a flow rate of 12.02 l/hr at room temperature. Then, while maintaining the internal pressure of the autoclave at 0.15 MPa by supplying 20% diluted fluorine gas at the same flow rate, a solution obtained by dissolving $CH_2ClCHClCH_2CH(CH_3)OCOCF(CF_3)$ $OCF_2CF_2CF_3$ (20 g) obtained in Example 2-2 in R-113 (100 g), was injected over a period of 6.0 hours.

Then, while maintaining the internal pressure of the autoclave at 0.15 MPa by supplying 20% diluted fluorine gas at the same flow rate, a R-113 solution having a benzene concentration of 0.04 g/ml was injected in an amount of 9 ml while raising the temperature from 25° C. to 40° C., whereupon the benzene solution inlet of the autoclave was closed, and stirring was continued for 0.3 hour.

Then, while maintaining the internal pressure of the autoclave at 0.15 MPa and the internal temperature of the reactor at 40° C., the above benzene solution was injected in an amount of 6 ml, whereupon the benzene solution inlet of the autoclave was closed, and stirring was continued for 0.3 hour. Further, the same operation was repeated 7 times. The total amount of benzene injected was 2.27 g, and the total amount of R-113 injected was 58 ml. Further, stirring was continued to 1.0 hour while supplying 20% diluted fluorine gas at the same flow rate.

Then, the internal pressure of the reactor was returned to normal pressure, and nitrogen gas was supplied for 1.5 hours. As a result of an analysis by GC-MS, formation of the above-identified compound was confirmed. From the quantitative analysis (internal standard: $C_6F_6$) by $^{19}F$-NMR, the yield of the above-identified compound was 43.7%.

$^{19}F$-NMR (282.7 MHz, solvent: $CDCl_3$, standard: $CFCl_3$) δ (ppm): −63.1 to −65.0 (2F), −75.5 to −76.5 (3F), −79.0 to −80.5 (1F), −81.9 (3F), −82.1 (3F), −86.0 to −88.0 (1F), −110.0 to −115.5 (2F), −130.0 (2F), −130.5 to −133.5 (2F), −135.0 to −138.0 (1F).

Example 2-4

Preparation Example for $CF_2ClCFClCF_2CF(CF_3)$ $OCOCF(CF_3)OCF_2CF_2CF_3$ by Fluorination Reaction Into a 3,000 ml autoclave made of nickel and having an external circulation tubular type reactor, $CF_3CF_2CF_2OCF$ $(CF_3)CF_2OCF(CF_3)COF$ (2,510 g) was put, circulated and stirred, and maintained at 25° C. At the gas outlet of the autoclave, a cooler maintained at −10° C. was installed. After supplying nitrogen gas for 2.0 hours, fluorine gas diluted to 50% with nitrogen gas (hereinafter referred to as 50% diluted fluorine gas) was supplied for two hours at a flow rate of 64.44 l/hr. Then, while supplying 50% diluted fluorine gas at the same flow rate, $CH_2ClCHClCH_2CH$ $(CH_3)OCOCF(CF_3)OCF_2CF_2CF_3$ (1,200 g) obtained in Example 2-2, was injected over a period of 24.0 hours. 1,400 g of the reaction crude liquid was withdrawn.

Then, while supplying 50% diluted fluorine gas at the same flow rate, $CH_2ClCHClCH_2CH(CH_3)OCOCF(CF_3)$ $OCF_2CF_2CF_3$ (1,200 g) was injected over a period of 24.0 hours. 1,400 g of the reaction crude liquid was withdrawn. The same operation was repeated 8 times, whereupon nitrogen gas was supplied for two hours. From the autoclave, the reaction crude liquid (2,220 g) was obtained.

Then, the reaction crude liquid (2,090 g) was put into the above autoclave, circulated and stirred, and maintained at 40° C. After supplying nitrogen gas for 2.0 hours, 50% diluted fluorine gas was supplied for two hours at a flow rate of 141.85 l/hr. Then, while supplying 50% diluted fluorine gas at the same flow rate, $CH_2ClCHClCH_2CH(CH_3)$ $OCOCF(CF_3)OCF_2CF_2CF_3$ (1,200 g) was injected over a period of 24.0 hours, and nitrogen gas was supplied for two hours. A reaction crude liquid (3,650 g) was obtained. Such reaction crude liquids were put together and analyzed by Coolon GC, whereby the yield of the above-identified compound was 83%.

Example 2-5

Preparation Example for $CF_2ClCFClCF_2COCF_3$ by Dissociation Reaction of Ester Linkage $CF_2ClCFClCF_2CF(CF_3)OCOCF(CF_3)OCF_2CF_2CF_3$ (24.8 g) obtained in Example 2-3 was charged into a flask together with KF powder (1.17 g) and heated at 130° C. for 2.0 hours and at 140° C. for 1.5 hours, in an oil bath, while stirring vigorously. At an upper portion of the flask, a reflux condenser adjusted at a temperature of 20° C., was installed. After cooling, a liquid sample (21.7 g) was recovered. The liquid sample was analyzed by GC-MS, whereby it was confirmed that $CF_3CF(OCF_2CF_2CF_3)COF$ and the above-identified compound were main products. The yield of the above-identified compound was determined by GC and found to be 85.0%.

Example 3

Preparation Example for $(CF_3)_2CO$

Example 3-1

Preparation Example for $(CH_3)_2CHOCOCF(CF_3)OCF_2CF$ $(CF_3)OCF_2CF_2CF_3$

A reaction was carried out in the same manner as in Example 1-1 except that $FCOCF(CF_3)OCF_2CF_2CF_3$ was changed to $FCOCF(CF_3)OCF_2CF(CF_3)OCF_2CF_2CF_3$ (61.0 g) to obtain a crude liquid. The crude liquid was washed twice with water (50 ml), dried over magnesium sulfate and then filtered to obtain $(CH_3)_2CHOCOCF(CF_3)OCF_2CF$ $(CF_3)OCF_2CF_2CF_3$ (64.0 g, GC purity: 98%).

Example 3-2

Preparation Example for $(CF_3)_2CFOCOCF(CF_3)$ $OCF_2CF(CF_3)OCF_2CF_2CF_3$ by Fluorination Reaction Into a 3,000 ml autoclave made of nickel and having an external circulation tubular type reactor, $CF_3CF_2CF_2OCF$ $(CF_3)CF_2OCF(CF_3)COF$ (2,534 g) was put, circulated and stirred, and maintained at 25° C. At the gas outlet of the autoclave, a cooler maintained at −10° C. was installed. After supplying nitrogen gas for 2.0 hours, 50% diluted fluorine gas was supplied for 2.0 hours at a flow rate of 41.97 l/hr. Then, while supplying 50% diluted fluorine gas at the same flow rate, $(CH_3)_2CHOCOCF(CF_3)OCF_2CF(CF_3)OCF_2CF_2CF_3$ (1,440 g) obtained in Example 3-1, was injected over a period of 24.0 hours. 1,700 g of the reaction crude liquid was withdrawn.

Then, while supplying 50% diluted fluorine gas at the same flow rate, $(CH_3)_2CHOCOCF(CF_3)OCF_2CF(CF_3)OCF_2CF_2CF_3$ (1,440 g) was injected over a period of 24.0 hours. The reaction crude liquid (1,700 g) was withdrawn. The same operation was repeated 5 times, whereupon nitrogen gas was supplied for two hours. From the autoclave, the reaction crude liquid (2,850 g) was obtained.

Then, the reaction crude liquid (2,500 g) was put into the above autoclave, circulated and stirred, and maintained at 25° C. After supplying nitrogen gas for 2.0 hours, 50% diluted fluorine gas was supplied for two hours at a flow rate of 41.97 l/hr. Then, while supplying 50% diluted fluorine gas at the same flow rate, $(CH_3)_2CHOCOCF(CF_3)OCF_2CF(CF_3)OCF_2CF_2CF_3$ (1,440 g) was injected over a period of 24.0 hours, and nitrogen gas was supplied for two hours. 4,190 g of the reaction crude liquid was obtained.

The desired product was quantified by $^{19}F$-NMR (internal standard: $C_6F_6$), whereby the yield of the above-identified compound was 94%.

$^{19}F$-NMR (376.0 MHz, solvent: $CDCl_3$, standard: $CFCl_3$) δ (ppm): −78.5 to −80.0 (7F), −80.7 (3F), −81.9 to −82.8 (8F), −84.8 to −86.3 (1F), −130.2 (2F), −132.2 (1F), −143.1 (1F), −145.4 (1F).

Example 3-3

Preparation Example for $(CF_3)_2CO$ by Dissociation Reaction of Ester Linkage

Example 3-3-1

A reaction was carried out in the same manner as in Example 1-3, except that the mixture (2.1 g) was changed to a mixture of $(CF_3)_2CFOCOCF(CF_3)OCF_2CF(CF_3)OCF_2CF_2CF_3$ and $(CF_3)_2CHOCOCF(CF_3)OCF_2CF(CF_3)OCF_2CF_2CF_3$ in a ratio of 8:2 (mass ratio) (hereinafter this mixture will be referred to as the fluorinated ester mixture, 10.0 g), and the NaF powder (0.02 g) was changed to KF powder (0.03 g). After cooling, a liquid sample (7.9 g) and a gas sample (1.9 g) were recovered. They were respectively analyzed by GC-MS, whereby it was confirmed that in the gas sample, the above-identified compound was the main product, and in the liquid sample, $FCOCF(CF_3)OCF_2CF(CF_3)OCF_2CF_2CF_3$ was the main product. The yield of the above-identified compound as calculated by GC in the same manner as in Example 1-3, was 95.2%. Further, from the liquid sample, $FCOCF(CF_3)OCF_2CF(CF_3)OCF_2CF_2CF_3$ (5.9 g) was obtained.

Example 3-3-2

Into an Inconel column (inner diameter: 14 mm, length 1 m), KF (10 to 20 mesh, 50 g) was packed and set in a salt bath, and the internal temperature of the salt bath was adjusted to 200° C. To this reactor, the fluorinated ester mixture was fed for two hours at a rate of 60 g/hr by means of a metering pump. At the outlet of the reactor, a reflux condenser adjusted at a temperature of −20° C. was installed, and the mixture was separated into a gas sample and a liquid sample. The gas sample (23.2 g) was recovered in a collecting container made of a fluorocarbon resin, and the liquid sample (95.8 g) was recovered in a glass trap. Both samples were respectively analyzed by GC-MS, whereby it was confirmed that in the gas sample, the above-identified compound was the main product, and in the liquid sample, $FCOCF(CF_3)OCF_2CF(CF_3)OCF_2CF_2CF_3$ was the main product. The yield of the above-identified compound as calculated in the same manner as in Example 1-3, was 96.5%. Further, from the liquid sample, $FCOCF(CF_3)OCF_2CF(CF_3)OCF_2CF_2CF_3$ (69.5 g) was obtained.

Example 3-3-3

A reaction was carried out in the same manner as in Example 3-3-2, except that KF was changed to activated carbon (10 to 20 mesh, 50 g), to obtain a gas sample (21.6 g) and a liquid sample (98.0 g). As a result of the analyses by GC-MS, it was confirmed that in the gas sample, the above-identified compound was the main product, and in the liquid sample, $FCOCF(CF_3)OCF_2CF(CF_3)OCF_2CF_2CF_3$ was the main product. The yield of the above-identified compound as calculated in the same manner as in Example 1-3, was 90.2%. Further, from the liquid sample, $FCOCF(CF_3)OCF_2CF(CF_3)OCF_2CF_2CF_3$ (64.6 g) was obtained.

Example 3-3-4

A reaction was carried out in the same manner as in Example 3-3-2, except that KF was changed to a catalyst having 10 mass % of KF supported on activated carbon (10 to 20 mesh, 50 g), to obtain a gas sample (22.3 g) and a liquid sample (97.6 g). As a result of the analyses by GC-MS, it was confirmed that in the gas sample, the above-identified compound was the main product, and in the liquid sample, $FCOCF(CF_3)OCF_2CF(CF_3)OCF_2CF_2CF_3$ was the main product. The yield of the above-identified compound as calculated in the same manner as in Example 1-3, was 93.1%. Further, from the liquid sample, $FCOCF(CF_3)OCF_2CF(CF_3)OCF_2CF_2CF_3$ (67.1 g) was obtained.

Example 3-3-5

A reaction was carried out in the same manner as in Example 3-3-2, except that KF was changed to a catalyst having 10 mass % of KF supported on activated alumina (10 to 20 mesh, 50 g), to obtain a gas sample (22.1 g) and a liquid sample (97.5 g). As a result of the analyses by GC-MS, it was confirmed that in the gas sample, the above-identified compound was the main product, and in the liquid sample, $FCOCF(CF_3)OCF_2CF(CF_3)OCF_2CF_2CF_3$ was the main product. The yield of the above-identified compound as calculated in the same manner as in Example 1-3, was 92.0%. Further, from the liquid sample, $FCOCF(CF_3)OCF_2CF(CF_3)OCF_2CF_2CF_3$ (66.2 g) was obtained.

Example 3-3-6

A reaction was carried out in the same manner as in Example 3-3-2, except that KF was changed to a catalyst having 10 mass % of KF supported on zirconia (10 to 20 mesh, 50 g), to obtain a gas sample (22.6 g) and a liquid sample (97.3 g). As a result of the analyses by GC-MS, it was confirmed that in the gas sample, the above-identified compound was the main product, and in the liquid sample, $FCOCF(CF_3)OCF_2CF(CF_3)OCF_2CF_2CF_3$ was the main product. The yield of the above-identified compound as calculated in the same manner as in Example 1-3, was 94.2%. Further, from the liquid sample, $FCOCF(CF_3)OCF_2CF(CF_3)OCF_2CF_2CF_3$ (67.6 g) was obtained.

Example 3-3-7

A reaction was carried out in the same manner as in Example 3-3-2, except that KF was changed to a catalyst having 10 mass % of KF supported on NaF (10 to 20 mesh, 50 g), to obtain a gas sample (23.3 g) and a liquid sample (96.5 g). As a result of the analyses by GC-MS, it was confirmed that in the gas sample, the above-identified compound was the main product, and in the liquid sample, FCOCF(CF$_3$)OCF$_2$CF(CF$_3$)OCF$_2$CF$_2$CF$_3$ was the main product. The yield of the above-identified compound as calculated in the same manner as in Example 1-3, was 97.1%. Further, from the liquid sample, FCOCF(CF$_3$)OCF$_2$CF(CF$_3$)OCF$_2$CF$_2$CF$_3$ (69.8 g) was obtained.

Example 4

Preparation Example for Perfluorocyclohexanone

Example 4-1

Preparation Example for CyOCOCF(CF$_3$)OCF$_2$CF$_2$CF$_3$

CyOH (20.0 g) was put into a flask and stirred while bubbling nitrogen gas. FCOCF(CF$_3$)OCF$_2$CF$_2$CF$_3$ (73.0 g) was dropwise added over a period of 1.5 hours while maintaining the internal temperature at from 28 to 30° C. After completion of the dropwise addition, stirring was continued for one hour at an internal temperature of 30° C., and a saturated sodium hydrogencarbonate aqueous solution (50 ml) was added at an internal temperature of at most 15° C.

The obtained crude liquid was subjected to liquid separation to obtain a fluorocarbon layer. Further, the fluorocarbon layer was washed twice with water (50 ml), dried over magnesium sulfate and then filtered to obtain a crude liquid. By distillation under reduced pressure, CyOCOCF(CF$_3$)OCF$_2$CF$_2$CF$_3$ (45.0 g) was obtained as a fraction of from 70 to 71° C./1.3 kPa (absolute pressure). The purity by GC was 99%. The NMR spectrum data were as follows.

$^1$H-NMR (300.4 MHz, solvent: CDCl$_3$, standard: CHCl$_3$) δ (ppm): 1.24 to 1.66 (m, 6H), 1.66 to 1.82 (m, 2H), 1.84 to 1.96 (m, 2H), 4.99 to 5.09 (m, 1H).

$^{19}$F-NMR (282.7 MHz, solvent: CDCl$_3$, standard: CFCl$_3$) δ (ppm): -79.7 (1F), -81.3 (3F), -82.2 (3F), -86.5 (1F), -129.5 (2F), -131.5 (1F).

Example 4-2

Preparation Example for Cy$^F$OCOCF(CF$_3$)OCF$_2$CF$_2$CF$_3$ by Fluorination Reaction Into a 200 ml autoclave made of nickel, R-113 (125 g) was put, stirred and maintained at 25° C. At the gas outlet of the autoclave, a cooler maintained at -10° C. and a layer packed with NaF pellets were installed in series. Nitrogen gas was supplied for 1.0 hour, and then, fluorine gas diluted to 20% with nitrogen gas, was supplied for 0.5 hour at a flow rate of 8.13 l/hr. Then, while supplying 20% diluted fluorine gas at the same flow rate and maintaining the pressure of the reactor at 0.15 MPa, was supplied for 0.5 hour. A solution obtained by dissolving the compound (5.0 g) obtained in Example 4-1 in R-113 (100 g), was injected over a period of 5.5 hours.

Then, while supplying 20% diluted fluorine gas at the same flow rate and maintaining the pressure of the reactor at 0.15 MPa, a R-113 solution having a benzene concentration of 0.01 g/ml was injected in an amount of 9 ml, while raising the temperature from 25° C. to 40° C., whereupon the benzene inlet of the autoclave was closed, and stirring was continued for 0.3 hour. Then, while maintaining the pressure of the reactor at 0.15 MPa and the internal temperature of the reactor at 40° C., the above-mentioned benzene solution (6 ml) was injected, and stirring was continued for 0.3 hour. Further, while maintaining the internal temperature of the reactor at 40° C., the above-mentioned benzene solution (6 ml) was injected, and stirring was continued for 0.3 hour. The same operation was repeated twice, and further while maintaining the internal temperature of the reactor at 40° C., the above-mentioned benzene solution (11 ml) was injected, and stirring was continued for further 1.0 hour. The total amount of benzene injected was 0.39 g, and the total amount of R-113 injected was 38 ml. Further, nitrogen gas was supplied for 1.0 hour. The desired product was quantified by $^{19}$F-NMR (internal standard: C$^6$F$^6$), whereby the yield of the above-identified compound was 85%.

$^{19}$F-NMR (376.0 MHz, solvent: CDCl$_3$, standard: CFCl$_3$) δ (ppm): -79.9 (1F), -82.0 (3F), -82.3 (3F), -87.2 (1F), -117.0 to -145.0 (11F), -130.2 (2F), -131.3 (1F).

Example 4-2

Preparation Example of Perfluorocyclohexanone

The product (3.5 g) obtained in Example 4-2 was charged into a flask together with KF powder (0.3 g) and heated at 120° C. for 3 hours in an oil bath, while stirring vigorously. Through a reflux condenser adjusted at a temperature of 20° C. at an upper portion of the flask, 2.7 g of a liquid sample was recovered. By GC-MS, it was confirmed that in the liquid sample, the above-identified compound and CF$_3$CF(OCF$_2$CF$_2$CF$_3$)COF are the main products.

Example 5

Preparation Example for Compound (5C)

Example 5-1

Preparation Example for the Following Compound (3C) by Esterification Reaction

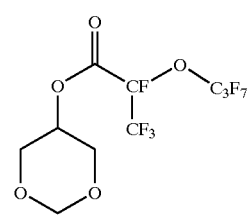

(3C)

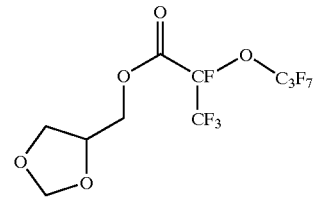

(3D)

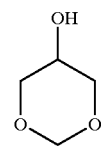

(1C)

(1D)

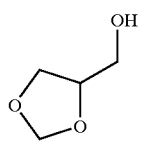

A mixture (10.0 g) of the compound (1C) and the compound (1D) in a ratio of 59:41 (molar ratio), and triethylamine (10.7 g) were put into a flask and stirred at an internal temperature of at most 10° C. FCOCF(CF$_3$)OCF$_2$CF$_2$CF$_3$ (35.1 g) was dropwise added over a period of 40 minutes, while maintaining the internal temperature at not higher than 10° C. After completion of the dropwise addition, stirring was continued for one hour at room temperature, and water (50 ml) was added, while maintaining the internal temperature at a level not exceeding 15° C. AK225 (100 ml) was added to the obtained crude liquid, followed by liquid separation to obtain the lower layer. Further, the lower layer was washed twice with water (50 ml), dried over magnesium sulfate and then, filtered to obtain a crude liquid. The crude liquid was concentrated by an evaporator, followed by distillation under reduced pressure to obtain a fraction (32.8 g) of from 59 to 62° C./0.4 kPa (absolute pressure). The GC purity was 99.6%.

From the NMR spectrum of the purified product, it was confirmed that a mixture of the compound (3C) and the compound (3D) was the main component, and their ratio was 59:41 (molar ratio).

Compound (3C):

$^1$H-NMR (300.4 MHz, solvent: CDCl$_3$, standard: TMS) δ (ppm): 3.97 (dd, J=4.1, 12.9 Hz, 2H), 4.07 (dd, J=2.6, 12.9 Hz, 2H), 4.82 (d, J=6.0 Hz, 1H), 4.92 to 4.96 (m, 1H), 4.94 (d, J=6.0 Hz, 1H).

$^{19}$F-NMR (282.7 MHz, solvent: CDCl$_3$, standard: CFCl$_3$) δ (ppm): −79.6 (1F), −81.3 (3F), −82.0 (3F), −86.5 (1F), −129.4 (2F), −131.5 (1F).

Compound (3D):

$^1$H-NMR (300.4 MHz, solvent: CDCl$_3$, standard: TMS) δ (ppm): 3.72 to 3.77 (m, 1H), 3.98 to 4.03 (m, 1H), 4.29 to 4.50 (m, 3H), 4.90 (s, 1H), 5.04 (s, 1H).

$^{19}$F-NMR (282.7 MHz, solvent: CDCl$_3$, standard: CFCl$_3$) δ (ppm): −79.8 (1F), −81.3 (3F), −82.1 (3F), −86.6 (1F), −129.5 (2F), −131.5 (1F).

Example 5-2

Preparation Example for the Following Compound (4C) by Fluorination Reaction (4C)

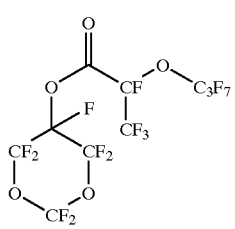

(4D)

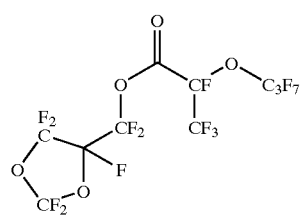

Into a 500 ml autoclave made of nickel, R-113 (312 g) was put, stirred and maintained at 25° C. At the gas outlet of the autoclave, a cooler maintained at 20° C., a layer packed with NaF pellets and a cooler maintained at −10° C. were installed in series. Further, a liquid returning line was installed to return a condensed liquid from the cooler maintained at −10° C. to the autoclave. Nitrogen gas was supplied for 1.0 hour, and then 20% diluted fluorine gas was supplied for one hour at a flow rate of 7.97 l/hr. Then, while supplying 20% diluted fluorine gas at the same flow rate, a solution obtained by dissolving the mixture (7.0 g) obtained in Example 5-1 in R-113 (140 g), was injected over a period of 5.1 hours.

Then, while supplying 20% diluted fluorine gas at the same flow rate and maintaining the pressure of the reactor at 0.15 MPa, a R-113 solution having a benzene concentration of 0.01 g/ml was injected in an amount of 9 ml, while raising the temperature from 25° C. to 40° C., whereupon the benzene inlet of the autoclave was closed and stirring was continued for 0.3 hour. Then, while maintaining the pressure of the reactor at 0.15 MPa and the internal temperature of the reactor at 40° C., 6 ml of the above-mentioned benzene solution was injected, and stirring was continued for 0.3 hour. Further, while maintaining the internal temperature of the reactor at 40° C., 6 ml of the above-mentioned benzene solution was injected, and stirring was continued for 0.3 hour. The same operation was repeated three times, and stirring was continued for further 0.7 hour. The total amount of benzene injected was 0.34 g, and the total amount of R-113 injected was 33 ml. Further, nitrogen gas was supplied for 1.0 hour. The desired product was quantified by $^{19}$F-NMR (internal standard: C$^6$F$^6$), whereby a mixture of the compound (3C) and the compound (4D) was obtained, and the total yield of the two compounds was 62%.

$^{19}$F-NMR (376.0 MHz, solvent: CDCl$_3$, standard: CFCl$_3$) δ (ppm): −52.7 (1F), −53.5 (1F), −79.3 to −80.6 (1F), −81.7 to −82.4 (6F), −82.6 to −85.8 (4F), −87.1 to −87.8 (1F), −130.2 (2F), −132.0 (1F), −139.8 (1F).

Example 5-3

Preparation Example for the Following Compound (5C) by Liquid Phase Pyrolytic Reaction of Ester Linkage The mixture (4.1 g) obtained in Example 5-2, was charged into a flask together with KF powder (0.3 g) and heated at 70° C. for one hour under 0.08 MPa (absolute pressure) in an oil bath, while stirring vigorously. Through a reflux condenser adjusted at a temperature of 20° C. at an upper portion of the flask, 0.6 g of a liquid sample was recovered. As a result of the analysis by GC-MS, it was confirmed that in the liquid sample, the following compound (5C) and the following compound (5D), and CF$_3$CF(OCF$_2$CF$_2$CF$_3$)COF, were the main products.

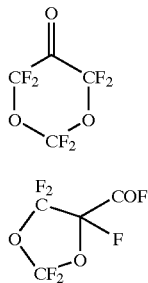

(5C)

(5D)

Industrial Applicability

According to the present invention, an industrially useful process for producing a fluorinated ketone, is provided. According to the process of the present invention, a fluorinated ketone can be produced in high yield by a short process from an inexpensive alcohol material. Further, according to the process of the present invention, it is possible to produce fluorinated ketones having various structures which used to be difficult to produce, by selecting the structure of the alcohol material. Further, the compound (5) having a —COF terminal, which is obtainable together with the fluorinated ketone by the method of the present invention, is a compound which can be a raw material for e.g. a fluorocarbon resin.

The entire disclosure of Japanese Patent Application No. 2000-261118 filed on Aug. 30, 2000 including specification, claims, and summary is incorporated herein by reference in its entirety.

What is claimed is:

1. A process for producing a fluorinated ketone of the following formula (5), which comprises:

reacting a compound of the following formula (3) having a fluorine content of at least 30 mass %, with fluorine in a liquid phase to obtain a compound of the following formula (4), and then, subjecting the ester linkage of the compound of the formula (4) to a dissociation reaction:

$$R^C COOCHR^A R^B \quad (3)$$

$$R^{CF} COOCFR^{AF} R^{BF} \quad (4)$$

$$R^{AF} R^{BF} C=O \quad (5)$$

wherein each of $R^A$ and $R^{AF}$ which may be the same or different, is a monovalent organic group, provided that when $R^A$ and $R^{AF}$ are different, $R^{AF}$ is a monovalent organic group formed by fluorination of $R^A$, and each of $R^B$ and $R^{BF}$ which may be the same or different, is a monovalent organic group, provided that when $R^B$ and $R^{BF}$ are different, $R^{BF}$ is a monovalent organic group formed by fluorination of $R^B$, and at least one of $R^{AF}$ and $R^{BF}$ is a fluorinated monovalent organic group; or $R^A$ and $R^B$ may be bonded to each other to form a bivalent organic group, and in such a case, $R^{AF}$ and $R^{BF}$ are bonded to each other to form a bivalent organic group, the bivalent organic group formed by $R^{AF}$ and $R^{BF}$ is a fluorinated bivalent organic group, the bivalent organic group formed by $R^A$ and $R^B$ and the bivalent organic group formed by $R^{AF}$ and $R^{BF}$ may be the same or different, provided that when they are different, the bivalent organic group formed by $R^{AF}$ and $R^{BF}$ is a group formed by fluorination; and each of $R^C$ and $R^{CF}$ which may be the same or different, is a monovalent organic group, provided that when $R^C$ and $R^{CF}$ are different, $R^{CF}$ is a monovalent organic group formed by fluorination of $R^C$, and provided that at least one of $R^A$, $R^B$ and $R^C$ is a group having an atom or an atomic group which can be substituted by a fluorine atom, and at least one of $R^A$, $R^B$ and $R^C$ is a group having a fluorine atom, wherein the dissociation reaction of the ester linkage is carried out in the absence of a solvent, using a solid nucleophilic agent.

2. The process according to claim 1, wherein $R^A$ is a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group, $R^{AF}$ is a group having $R^A$ perfluorinated, $R^B$ is a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group, $R^{BF}$ is a group having $R^B$ perfluorinated, and $R^C$ and $R^{CF}$ are the same and each a group having a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group, perfluorinated.

3. The process according to claim 1, wherein $R^A$ and $R^B$ are bonded to each other to form a bivalent saturated hydrocarbon group, a partially halogenated bivalent saturated hydrocarbon group, an etheric oxygen atom-containing bivalent saturated hydrocarbon group or a partially halogenated (etheric oxygen atom-containing bivalent saturated hydrocarbon) group, $R^{AF}$ and $R^{BF}$ are a group having the group formed by $R^A$ and $R^B$, perfluorinated, and $R^C$ and $R^{CF}$ are the same and each a group having a monovalent saturated hydrocarbon group, a partially halogenated monovalent saturated hydrocarbon group, an etheric oxygen atom-containing monovalent saturated hydrocarbon group or a partially halogenated (etheric oxygen atom-containing monovalent saturated hydrocarbon) group, perfluorinated.

4. The process according to claim 1, wherein the molecular weight of the compound of the formula (3) is from 200 to 1,000.

5. The process according to claim 1, wherein the carbon number of $R^C$ is from 2 to 10.

6. The process according to claim 1, wherein the dissociation reaction of the ester linkage is carried out by heating the compound of the formula (4) in a liquid phase at from 50° C. to 300° C.

7. The process according to claim 1, wherein the dissociation reaction of the ester linkage is carried out by reacting the compound of the formula (4) in a liquid phase in the presence of a nucleophilic agent.

8. The process according to claim 1, wherein the dissociation reaction of the ester linkage is carried out by heating the compound of the formula (4) in a gas phase at from 150° C. to 250° C.

9. The process according to claim 1, wherein the dissociation reaction of the ester linkage is carried out by heating the compound of the formula (4) in a gas phase at from 150° C. to 250° C. in at least one of a reaction tube packed with glass, an alkali metal salt, an alkaline earth metal salt or activated carbon.

10. The process according to claim 1, wherein the dissociation reaction of the ester linkage is carried out by heating the compound of the formula (4) in a gas phase at from 150° C. to 250° C. in a reaction tube packed with potassium fluoride.

11. The process according to claim 1, wherein when the compound of the formula (3) is reacted with fluorine in a liquid phase, at least one compound selected from a compound of the following formula (2), the compound of the formula (4), the fluorinated ketone of the formula (5) and a compound of the following formula (6), is used as the liquid phase:

$$R^C COX \quad (2)$$

$$R^{CF} COF \quad (6)$$

wherein $R^C$ and $R^{CF}$ are as defined above.

12. The process according to claim 1, wherein the compound of the formula (3) is a compound obtained by reacting a compound of the following formula (1) and a compound of the following formula (2):

$$HOCHR^A R^B \quad (1)$$

$$R^C COX \quad (2)$$

wherein $R^A$, $R^B$ and $R^C$ are as defined above, and X is a halogen atom.

13. The process according to claim 1, wherein a compound of the following formula (6) is obtained together with the fluorinated ketone of the formula (5) from the reaction product of the dissociation reaction of the ester linkage:

$$R^{CF} COF \quad (6)$$

wherein $R^{CF}$ is as defined above.

14. The process according to claim 12, wherein the compound of the formula (2) which is reacted with the compound of the formula (1), is a compound of the following formula (6), which is obtained together with the fluorinated ketone of the formula (5) from the reaction product of the dissociation reaction of the ester linkage:

$$R^{CF} COF \quad (6)$$

wherein $R^{CF}$ is as defined above.

15. The process according to claim 1, wherein the compound of formula (3) has a fluorine content of from 30 mass % to 86 mass %.

16. The process according to claim 15, wherein the compound of formula (3) has a fluorine content of from 30 mass % to 76 mass %.

17. The process according to claim 1, wherein the nucleophilic agent is selected from the group consisting of KF, NaF, NaHF$_2$, CsF, and combinations thereof.

18. The process according to claim 12, wherein the mole ratio of the compound (2) to the compound (1) is from 0.5 to 5.

19. The process according to claim 12, wherein the mole ratio of the compound (2) to the compound (1) is from 1 to 2.

20. The process according to claim 1, wherein said reacting occurs at a temperature ranging from −50° C. to +100° C.

21. The process according to claim 1, wherein said reacting occurs at a temperature ranging from −20° C. to +50° C.

22. The process according to claim 18, wherein the nucleophilic agent is selected from the group consisting of KE, NaF, NaHF$_2$, CsF, and combinations thereof.

23. The process according to claim 19, wherein the nucleophilic agent is selected from the group consisting of KF, NaF, NaHF$_2$, CsF, and combinations thereof.

* * * * *